United States Patent [19]

Loyer

[11] 4,148,317

[45] Apr. 10, 1979

[54] REDUCED LENGTH TAMPON-APPLICATOR ASSEMBLY

[75] Inventor: Michael Loyer, Somerville, N.J.

[73] Assignee: Personal Products Company, Milltown, N.J.

[21] Appl. No.: 833,201

[22] Filed: Sep. 14, 1977

[51] Int. Cl.² ............................................. A61F 15/00
[52] U.S. Cl. .................................... 128/263; 128/270; 128/285
[58] Field of Search .......... 128/260, 263, 270, 290 R, 128/290 H, 284, 285, 269, 130, 271

[56] References Cited

U.S. PATENT DOCUMENTS

| 2,155,285 | 4/1939 | Wilkerson | 128/285 |
| 3,034,508 | 5/1962 | Nalle, Jr. | 128/263 |
| 3,086,527 | 4/1963 | Forrest | 128/263 |
| 3,101,713 | 8/1963 | Sargent | 128/263 |
| 3,983,875 | 10/1976 | Truman | 128/285 |

*Primary Examiner*—Robert W. Michell
*Attorney, Agent, or Firm*—Jason Lipow

[57] ABSTRACT

A tampon-applicator assembly of reduced length is provided comprising a generally cylindrical absorbent tampon having a proximal end and a distal end and a tampon bore within the tampon extending from said distal end toward the proximal end. A retainer is affixed to the distal end and has a bore therethrough coaxial with the tampon bore. A plunger is provided and adapted to be stored within the bore prior to use and to be reciprocated out of the tampon bore when the tampon is to be inserted. Screw threads or longitudinal splines are provided for the plunger to bear against the retainer. The retainer bears against the tampon when insertion pressure is applied. After insertion, the plunger and the retainer are removable.

11 Claims, 11 Drawing Figures

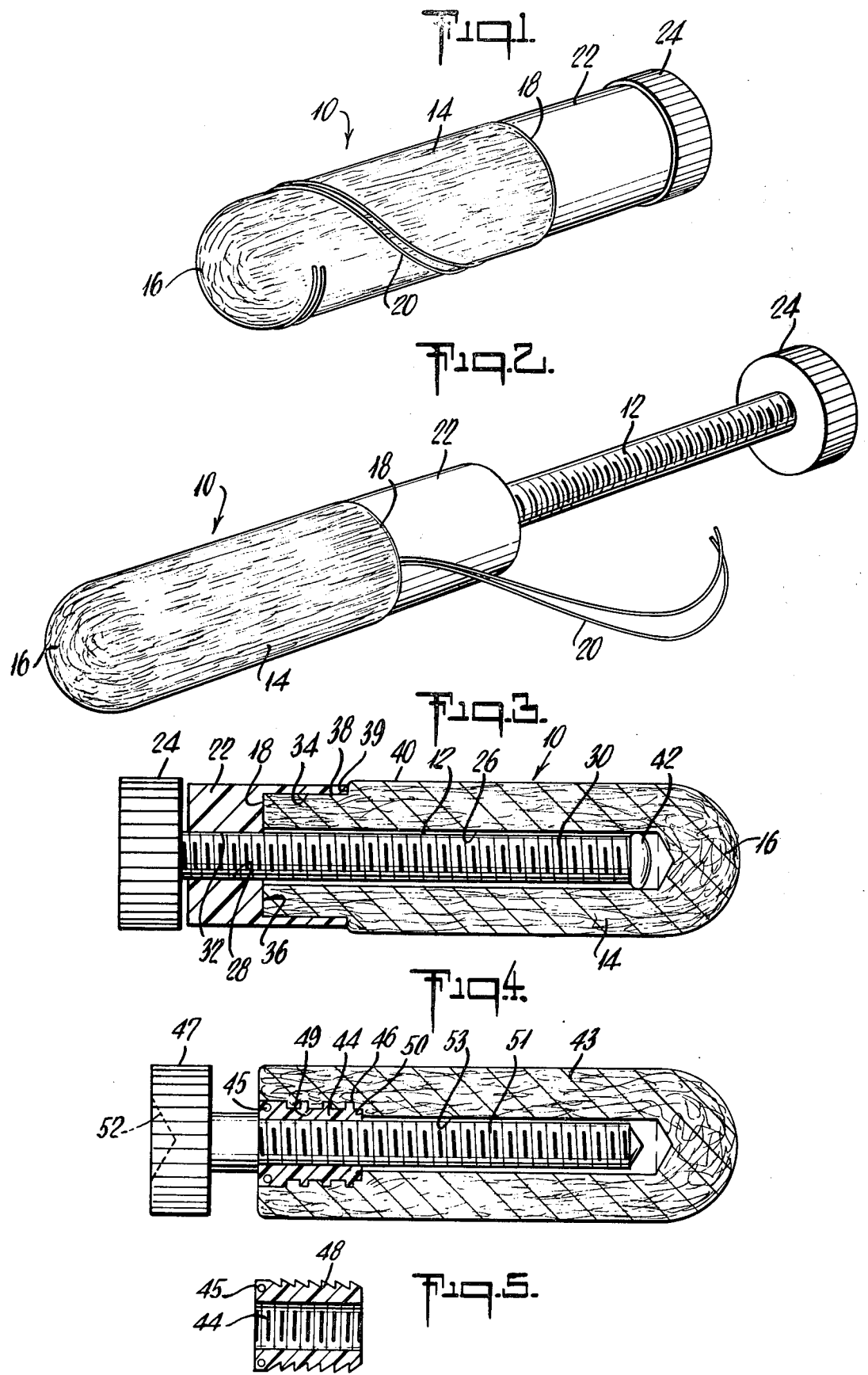

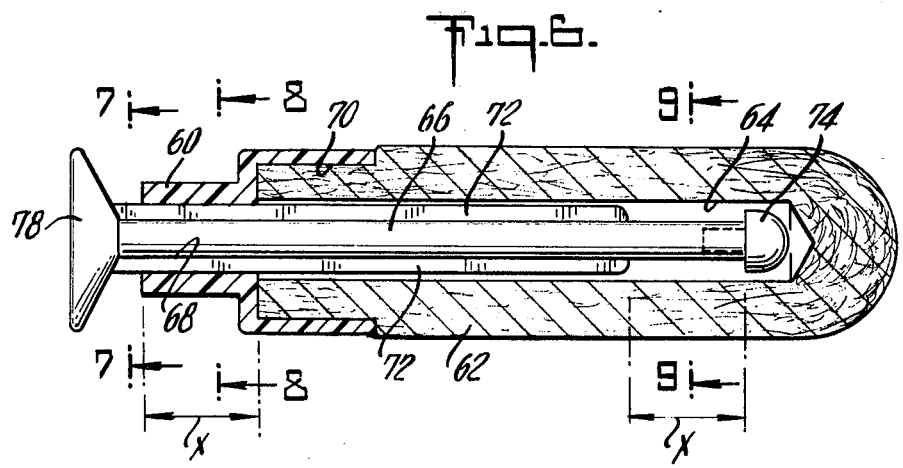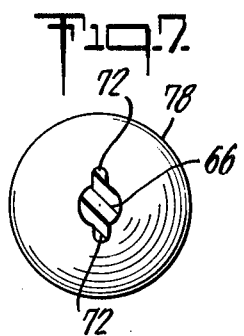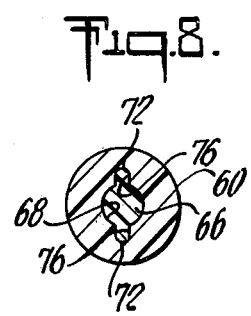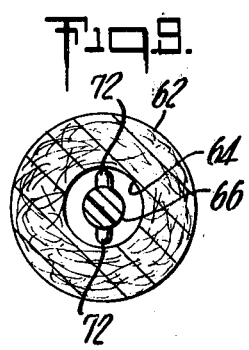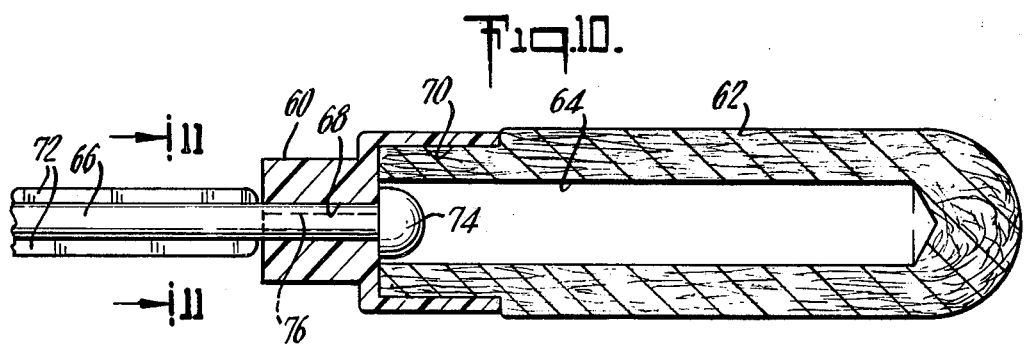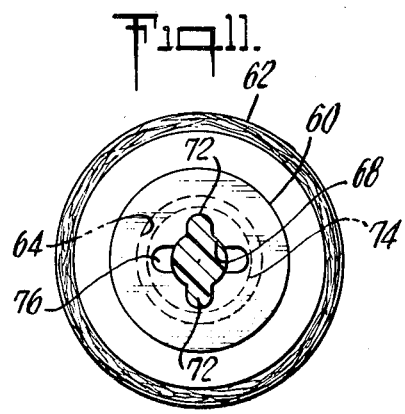

REDUCED LENGTH TAMPON-APPLICATOR ASSEMBLY

BACKGROUND OF THE INVENTION

This invention relates to a tampon-applicator assembly and is particularly directed toward such a combination having a reduced length.

Several applicators for introducing catamenial tampons intervaginally are already available. The type in widest use comprises an open ended tubular holder containing the tampon combined with a plunger adapted to slideably expel the tampon from the holder. The plunger is also generally tubular, though smaller in diameter than the holder and is telescopically positioned therein so that by moving the plunger into one end of the holder, the tampon may be ejected from the opposite end. The holder is, of necessity, longer than the tampon and to insure complete ejection of the tampon from the holder, the plunger is likewise, longer. Consequently, the overall length of the holder and plunger assembly is always more than twice the length of the tampon.

Another type of prior tampon-applicator assembly is exemplified in U.S. Pat. No. 3,481,335 issued on Dec. 2, 1969 to F. W. Bentlich; U.S. Pat. No. 3,595,236, issued on July 27, 1971 to V. A. Corrigen et al and U.S. Pat. No. 3,683,912, issued on Aug. 15, 1972 to V. A. Olson et al. These comprise a tampon having a bore in the distal end (i.e., the end opposite the proximal end which is first inserted into the vagina) to accommodate the initial portion of a rigid, stick-like support which is held by the user when inserting the tampon. Again the stick-like support must extend out of the base at least the length of the tampon and hence the assembly of tampon and support is at least twice the length of the tampon. It will be appreciated by those skilled in the art that the support used to insert the tampon bears directly upon the body of the tampon during insertion. Accordingly, it is highly undesirable to have the stick-like support inserted into the distal end of the tampon for any great length as there is the danger of the support piercing through the proximal end of the tampon and injuring the user. For this additional reason, a large portion of the support must extend outside the bore and hence add to the size of the tampon applicator assembly.

Several drawbacks are associated with such prior applicators. To provide sufficient tampon and applicator assemblies for a menstrual period, it is customary to package a number of them, e.g., ten, in a single container. From the foregoing description of prior applicators, it is apparent that the tampon applicator and hence the containers used to package them are comparatively large with respect to the size of the article, i.e., the tampon, ultimately used by the consumer. The necessity for large containers greatly adds to the cost of the marketed product, such added cost being particularly important in products of the type herein considered which are intended for a single use and are then discarded. Accordingly, there is an economic incentive for a reduction in product size.

Moreover, a size reduction is advantageous from both a convenience and an aesthetic point of view. The product should be small enough to be conveniently carried in a woman's purse. From an aesthetic viewpoint, a shorter product is less noticeable.

To avoid the problem of excessive length, it has been suggested (see U.S. Pat. No. 3,086,527 issued on Apr. 23, 1963 to D. C. Forrest) that the plunger and holder be provided in unassembled form and packaged side by side, thereby substantially reducing the overall length of the package. While such a system would in fact greatly reduce packaging requirements, the complexity in manufacturing, coupled with the difficulty and inconvenience to the consumer, has made such products both uneconomical and undesirable.

Accordingly, there is need for a tampon-applicator assembly which is not substantially longer than the tampon itself and is economical to produce and simple to use.

SUMMARY OF THE INVENTION

In accordance with this invention, a tampon-applicator assembly is provided comprising a generally cylindrical absorbent tampon having a proximal end, i.e., the end first inserted into the vagina and a distal end, i.e., the end opposite the proximal end. A tampon bore is provided within the tampon which extends from the distal end toward the proximal end and is of sufficient length to accommodate the major portion of an elongated plunger. A retainer is affixed to the distal end of the tampon and has a retainer bore therethrough which is coaxial with the tampon bore. A longitudinally extending plunger is provided, adapted to be stored substantially within the retainer and tampon bores prior to use and to be reciprocated axially out of the tampon bore in the direction of from the proximal end toward the distal end when the tampon is to be inserted. First means are provided for the plunger to bear against the retainer when pressure is applied to the plunger, as when inserting the tampon. Second means are provided for the retainer to bear against the tampon when such inserting pressure is applied. Because the plunger at no time bears against the tampon itself, this application may be safely used with tampons of all kinds including even those of relatively low density.

In a specific embodiment such first means comprise having at least a portion of said plunger provided with threads adapted to engage threads within the retainer bore. The plunger may be reciprocated out of its stored position within the tampon bore by simply unscrewing the plunger in the direction which will advance the plunger away from the proximal end of the tampon. Having achieved a sufficient degree of advancement for insertion, the engaged threads will provide the bearing surface for the plunger to bear against the retainer when insertion force is applied.

In a second embodiment such first means comprise providing the plunger with one or more longitudinal splines which are slideably engaged within a keyway provided in the retainer. The proximal end of the plunger is free of such splines for a distance approximately equal to the longitudinal length ot the retainer. A head is provided at the extreme proximal end of the plunger. In use, the plunger is axially reciprocated from its stored position in the tampon bore toward the distal end of the tampon until the spline-free portion is within the retainer bore, the head stopping further axial reciprocation. The plunger is then rotated so that the splines are out of registry with the keyway in the retainer and instead, upon application of inserting pressure, bears against the distal end of the retainer.

In a first embodiment of the second means for having the retainer bear against the tampon under the influence of inserting pressure, the distal end of the tampon is provided with a reduced diameter section thus forming a shoulder between this reduced diameter section and the remainder of the tampon. The proximal end of the retainer is provided with tampon receiving bore of inside diameter approximately that of the reduced diameter section of the tampon and is frictionally fitted over this section thus bearing against the distal end of the tampon and the shoulder upon application of inserting pressure.

In a second embodiment of the second means, the tampon is provided at its distal end with a retainer receiving bore into which the retainer is engaged by means of adhesive, barbs, threads or the like. The retainer receiving bore is preferably of greater diameter than the tampon bore, forming a shoulder within the tampon against which the receiver bears under the influence of inserting pressure.

BRIEF DESCRIPTION OF THE DRAWINGS

FIG. 1 is a perspective view of a tampon-applicator assembly of this invention shown with the plunger in a stored position;

FIG. 2 is a perspective view of the tampon-applicator assembly shown in FIG. 1 with the plunger in the insertion position;

FIG. 3 is a longitudinal cross-sectional view of the tampon applicator assembly of FIG. 1;

FIG. 4 is a longitudinal cross-sectional view of a second embodiment of the tampon-applicator assembly of FIG. 1;

FIG. 5 is a longitudinal cross-sectional view of another embodiment of the retainer for use in the tampon-applicator assembly of this invention;

FIG. 6 is a longitudinal cross-section view of still another embodiment of the tampon-applicator assembly of this invention, with the plunger shown in the stored position;

FIG. 7 is a cross-sectional view of the plunger taken through line 7—7 of FIG. 6;

FIG. 8 is a cross-sectional view of the plunger and retainer taken through line 8—8 of FIG. 6;

FIG. 9 is a cross-sectional view of the plunger and tampon taken through line 9—9 of FIG. 6;

FIG. 10 is a longitudinal, cross-sectional view of the tampon-applicator assembly of FIG. 6 rotated ninety degrees and with the plunger shown in the insertion position; and FIG. 11 is a cross-sectional view of the plunger taken through line 11—11 of FIG. 10.

DETAILED DESCRIPTION OF THE INVENTION

Referring now to FIGS. 1 and 2 shown therein in perspective view is an embodiment of the tampon applicator assembly 10 illustrated with the plunger 12 in the stored position and insertion position, respectively. A catamenial tampon 14 is provided which may be of the conventional type comprising an absorbent material formed into a cylindrical shape and provided at its proximal end 16 with a domed shape for easier insertion and at its distal end 18 with a withdrawal string 20 for removing the used tampon. For descriptive purpose herein the terms proximal end and distal end are used, with respect to an element, to denote parts of the element nearest to and furthest from, respectively, the vaginal orifice when the tampon is being inserted.

In accordance with this invention, a retainer 22 is affixed to the distal end 18 of the tampon 14 and the plunger 12 passes therethrough and into the tampon body for storage and out of the tampon body when ready for insertion. As can be seen from FIG. 1, the tampon assembly 10, with the plunger 12 in the stored position is just somewhat longer than the tampon 14 itself and hence may be packaged easily and carried conveniently by the user in her purse. On the other hand, with the plunger in the insertion position, as is shown in FIG. 2, a sufficient length is provided for safely and accurately inserting the tampon into the vaginal vault. To aid in reciprocating the plunger 12 into the insertion position and to facilitate insertion, the distal end of the plunger is provided with an elongated knurled end 24.

Referring now to FIG. 3, shown therein, in longitudinal cross section, is the tampon-applicator assembly 10 of FIG. 1, with the plunger 12 in the stored position. The tampon 14 is provided with a tampon bore 26 which extends from the distal end 18 of the tampon toward its proximal end 16. While the tampon bore 26 does not extend for the entire length of the tampon, it is meant, preferably, to provide storage for the major portion of the plunger 12 and, therefore, extends for a major portion of the length of the tampon.

The retainer 22, affixed to the distal end 18 of the tampon is provided with a retainer bore 28, coaxial with the tampon bore 26. The plunger is, therefore, adapted to be stored within both of these bores prior to use and to be reciprocated in a direction of from the proximal end of the tampon toward the distal end of the tampon to reach the insertion position, as illustrated in FIG. 2.

First means are provided for the plunger to bear against the retainer when pressure is applied to the plunger in the direction of the proximal end, i.e., during tampon insertion. In the embodiment illustrated in FIG. 3, these first means comprise having the longitudinal length of the plunger provided with threads 30 adapted to engage threads 32 in the inside surface of the retainer bore 28. Accordingly, the plunger may be rotated, as by gripping and rotating the enlarged, knurled end 24 to advance the plunger axially out of the tampon bore until the plunger is in the insertion position as shown in FIG. 2. Thereafter, the tampon may be inserted into the vagina by applying pressure to the end 24. The engaged threads 30 and 32 will provide bearing surfaces for the plunger to bear against the retainer and not against the tampon.

Second means are provided for the retainer to bear against the tampon upon the application of insertion pressure to the plunger. In the embodiment shown in FIG. 3, these means comprise providing, in the proximal end of the retainer, a bearing bore 34 having a diameter larger than the retainer bore 28 and extending only partially toward the distal end of the retainer. The retainer is then affixed to the tampon by inserting the distal end of the tampon into this bearing bore 34 and is held there by friction. Accordingly, when insertion force is brought to bear against the plunger, this force is transmitted to the retainer and to the distal end of the tampon 18 through the bottom surface 36 of bearing bore 34. To reduce the size of the bearing bore and to provide smooth surfaces at the distal end of the tampon, it is preferred, as is illustrated in FIG. 3, that the distal portion of the tampon be provided with a reduced diameter section 38 which will form a shoulder 39 at the interface between the reduced diameter section 38 and the remaining section 40 of the tampon. The diameter of the bearing bore 34 may be approximately equal to that of the reduced diameter section 38 and the outside diameter of the retainer may be effectively the same diameter as (or even less than) the major portion 40 of the tampon, presenting a smooth outside surface for the assembly.

In connection with the embodiment shown in FIG. 3, both the plunger and retainer are removed after the tampon is inserted. This can be accomplished by providing an enlarged head 42 at the proximal end of the plunger having a diameter larger than the retainer bore 28. This will prevent the advancing of the plunger completely out of the retainer bore and instead, after insertion, when a force is brought to bear on the plunger in a direction of from the proximal end to the distal end, the head will bear against the retainer (specifically at the bottom surface 36 of the bearing bore 34) and overcome the frictional force holding the retainer to the tampon, whereupon both the retainer and plunger may be removed from the tampon. The enlarged head 42 may be specially molded or may instead by simply one or more distorted threads formed at the proximal end of the plunger after assembly of plunger and retainer.

It will be understood however that, if desired, the enlarged head 42 may be eliminated and, after tampon has been inserted, the plunger may be further advanced so as to be totally withdrawn from the tampon and retainer bores leaving both the tampon and retainer in the vagina.

FIGS. 4 and 5 illustrate alternatives for the second means provided for having the retainer bear against the tampon upon application of insertion pressure to the plunger. In these embodiments, the outside diameter of the retainer 44 is less than that of the tampon 43 and the outside surface is provided with one or more circumferencial projections which may be rings 46 as illustrated in FIG. 4 or barbs 48 as illustrated in FIG. 5. Alternatively, the circumferencial projections may be threads. In any event, the retainer 44 is emplaced within the body of the tampon at the distal end thereof by force fitting, screwing into the tampon or any other suitable method. To aid in fabricating the tampon-applicator assembly, the enlarged knurled end 47 of the plunger 51 has been provided with a socket 52 adapted to accommodate a tool for assembling and driving both the plunger and the retainer into the tampon. A right frictional fit will hold the retainer in place and when insertion pressure is applied, this tight fit in combination with the circumferential projections will provide bearing surfaces to transmit the pressure from the retainer to the tampon. Preferably the tampon is provided with an enlarged tampon bore 49 at its distal end having a diameter approximately equal to the outside diameter of the retainer 44, and a length sufficient to accommodate the retainer. At the interface between the enlarged tampon bore 49 and the tampon bore 53, a shoulder 50 results which will also provide a surface for the retainer to bear against in transmitting insertion pressure to the tampon. As shown in this embodiment, the retainer is provided with holes 45 molded therein to accommodate a withdrawal string (not shown).

To insert, the plunger is reciprocated into the insertion position. Color coding or other indicia may be provided on the plunger to guide the user as to the proper distance to so reciprocate the plunger. After insertion, the plunger may be removed and the retainer will remain within the tampon.

Illustrated in FIGS. 6 through 9 is another embodiment for the first means for the plunger to bear against the retainer upon application of insertion pressure. Shown therein is a retainer 60 and tampon 62 having similar structure as compared to the embodiments shown in FIGS. 3 and 4 with a plunger 66 illustrated in the stored position. The tampon is provided with a tampon bore 64 for storing the plunger 66. The retainer 60 is provided with a retainer bore 68 and a bearing bore 70. The plunger 66 is provided with an enlarged end 78 for facilitating insertion. In accordance with this embodiment, in lieu of threads, the plunger 66 is provided with one or more splines 72 spaced circumferentially and extending longitudinally on the outside surface of the plunger from the distal end of the plunger to a point near the proximal end. The proximal end is provided with an enlarged head 74 and the distance between the head and the proximal termination of the splines (designated in the drawing by the dimension X) is essentially equal to the length of the retainer bore. This spline-free portion of the plunger is best illustrated in FIG. 9. As can be best viewed in FIG. 7, a cross-sectional view of the plunger, the splines (two are illustrated) are spaced about the cross-sectional circumference of the plunger. FIG. 8 is a cross-sectional view taken through the retainer when the plunger is in a stored position and hence the splined section thereof passes through the retainer. As can be seen in this FIG. 8, the retainer is provided with keyways 76, equal in number to the splines and adapted to have the splines be slideably fitted therein. In use, the plunger is reciprocated in a direction from the proximal end toward the distal end and into the insertion position which is reached when the enlarged head 74 bears against the retainer. This position is illustrated in FIGS. 10 and 11. Referring to FIG. 10, it will be noted that with the plunger in the insertion position, only the spline-free portion of the plunger resides in the retainer bore 68. Having reciprocated the plunger to this position, the plunger is now rotated so that the splines are out of registry with the keyholes 76 in the retainer. Accordingly, insertion pressure may now be applied to the plunger and this pressure will be transmitted to the retainer by having the ends of the spline bear against the distal end of the retainer.

The retainer and plunger of this invention may be manufactured from any suitably rigid material such a moldable synthetic polymers or material polymers such as rubber, with the material of choice being polypropylene or polyethylene.

What is claimed is:

1. A tampon-applicator assembly comprising:
   a generally cylindrical absorbent tampon having a proximal end and a distal end;
   a tampon bore within the tampon, longitudinally extending from said distal end toward said proximal end;
   a retainer affixed to said distal end and having a retainer bore therethrough coaxial with said tampon bore;
   a longitudinally extending plunger adapted to be stored substantially within said bores prior to use and to be reciprocated substantially out of said tampon bore in the direction of from the proximal end toward the distal end when the tampon is to be inserted;
   first means for said plunger to bear against said retainer when pressure is applied to said plunger in the direction of toward the proximal end during insertion; and
   second means for said retainer to bear against said tampon when pressure is applied to said plunger in the direction of toward the proximal end during insertion.

2. The tampon-applicator assembly of claim 1 wherein said first means comprise having the longitudinal length of the plunger provided with threads adapted to engage threads in the inside surface of the retainer bore whereby said engaged threads will provide bearing surfaces for the plunger to bear against the retainer when pressure is applied during insertion.

3. The tampon-applicator assembly of claim 1 wherein said first means comprise: having said plunger provided with one or more circumferentially spaced splines extending from the distal end of said plunger toward the proximal end;
  providing, at said proximal end of said plunger, an enlarged head, said splines terminating at a distance from said enlarged head at least equal to the longitudinal length of said retainer bore;
  said retainer bore having keyways adapted to slidably engage said splines when said plunger is in a stored position;
  whereby said plunger may be reciprocated out of said stored position into an insertion position and rotated about its axis whereupon said splines, will be out of registry with said keyways and bear against said retainer when pressure is applied during insertion.

4. The tampon-applicator assembly of claim 1 wherein said second means comprise:
  providing, in the proximal end of said retainer, a bearing bore having a diameter larger than the retainer bore and extending only partially toward the distal end of said retainer, said bearing bore having a bottom surface; the distal end of said tampon being inserted into said bearing bore and against said bottom surface whereby said retainer will bear against the distal end of said tampon when pressure is applied during insertion.

5. The tampon-applicator assembly of claim 4 wherein the distal portion of the tampon has a reduced diameter whereby a shoulder is formed between said distal portions and the remainder of the tampon and said bearing bore having a diameter approximately equal to said reduced diameter.

6. The tampon-applicator assembly of claim 4 wherein the proximal end of the plunger is provided with an enlarged head having a diameter larger than said retainer bore to preclude said plunger from passing out of said retainer bore.

7. The tampon-applicator assembly of claim 1 wherein said second means comprise: the outside diameter of said retainer being less than the diameter of said tampon; the outside surface of said retainer being provided with circumferencial projections, and said retainer being emplaced within the body of the tampon at the distal end whereby upon application of insertion pressure, said retainer and said circumferencial projections will bear against the distal end of said tampon.

8. The tampon-applicator assembly of claim 7 wherein the distal end of said tampon is provided with an enlarged tampon bore of a length sufficient to accommodate said retainer.

9. The tampon-applicator assembly of claim 7 wherein said circumferential projections are rings.

10. The tampon-applicator assembly of claim 7 wherein said circumferential projections are barbs.

11. The tampon-applicator assembly of claim 7 wherein said circumferencial projections are threads.

* * * * *